(12) United States Patent
Knapp et al.

(10) Patent No.: US 12,137,902 B2
(45) Date of Patent: Nov. 12, 2024

(54) ADAPTIVE ANTI-TWITCH ALGORITHM FOR POWERED SURGICAL DEVICES

(71) Applicant: Covidien LP, Mansfield, MA (US)

(72) Inventors: Robert Knapp, Middlebury, CT (US); Matthew Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 645 days.

(21) Appl. No.: 16/442,030

(22) Filed: Jun. 14, 2019

(65) Prior Publication Data
US 2020/0029960 A1    Jan. 30, 2020

Related U.S. Application Data

(60) Provisional application No. 62/702,995, filed on Jul. 25, 2018.

(51) Int. Cl.
*A61B 17/068* (2006.01)
*A61B 17/115* (2006.01)
(Continued)

(52) U.S. Cl.
CPC .......... *A61B 17/068* (2013.01); *A61B 17/115* (2013.01); *A61B 17/282* (2013.01);
(Continued)

(58) Field of Classification Search
CPC ... A61B 17/068; A61B 17/115; A61B 17/282; A61B 2017/00221; A61B 2017/00393;
(Continued)

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CA | 2824590 A1 | 4/2014 |
| CN | 101683284 A | 3/2010 |

(Continued)

OTHER PUBLICATIONS

European Examination Report dated Oct. 7, 2020 issued in corresponding EP Appln. No. 19 188 040.0.

(Continued)

*Primary Examiner* — Alentin Neacsu
*Assistant Examiner* — Mary C Hibbert-Copeland (57) ABSTRACT

A surgical device includes a handle assembly having a controller; a first motor; and a second motor. The surgical device also includes an adapter assembly having: a tubular housing defining a longitudinal axis having a proximal end portion configured to couple to the handle assembly, and a distal end portion; a first actuation assembly disposed within the tubular housing and coupled to the first motor; and a second actuation assembly disposed within the tubular housing and coupled to the second motor. The surgical device further includes an end effector configured to couple to the distal end portion of the adapter assembly. The end effector is coupled to the first actuation assembly that articulates the end effector about an articulation axis that is perpendicular to the longitudinal axis. The end effector also includes a flexible drive beam coupled to the second actuation assembly and movable axially by the second actuation assembly. The controller is configured to maintain an initial articulation position of the end effector in response to axial movement of the flexible drive beam.

9 Claims, 8 Drawing Sheets

(51) Int. Cl.
*A61B 17/28* (2006.01)
*A61B 17/00* (2006.01)
*A61B 17/072* (2006.01)

(52) U.S. Cl.
CPC ............... *A61B 2017/00221* (2013.01); *A61B 2017/00393* (2013.01); *A61B 2017/00398* (2013.01); *A61B 2017/00464* (2013.01); *A61B 2017/00473* (2013.01); *A61B 2017/00486* (2013.01); *A61B 2017/00734* (2013.01); *A61B 2017/07257* (2013.01); *A61B 2017/07271* (2013.01)

(58) Field of Classification Search
CPC ............ A61B 2017/00398; A61B 2017/00464; A61B 2017/00473; A61B 2017/00486; A61B 2017/00734; A61B 2017/07257; A61B 2017/07271
USPC .......................................... 227/175.1–176.1
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |

(56) References Cited

U.S. PATENT DOCUMENTS

| | | |
|---|---|---|
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |

(56) References Cited

U.S. PATENT DOCUMENTS

| | | |
|---|---|---|
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |

(56) References Cited

U.S. PATENT DOCUMENTS

| | | | |
|---|---|---|---|
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0036890 A1 | 2/2011 | Ma |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0089131 A1* | 4/2012 | Zemlok ............ A61B 17/072 606/1 |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2017/0172573 A1 | 6/2017 | Viola et al. |
| 2018/0110518 A1 | 4/2018 | Overmyer et al. |
| 2018/0360446 A1* | 12/2018 | Shelton, IV ........ A61B 17/1114 |
| 2019/0183503 A1* | 6/2019 | Shelton, IV ..... A61B 17/07207 |

FOREIGN PATENT DOCUMENTS

| | | |
|---|---|---|
| CN | 102648864 A | 8/2012 |
| CN | 107635488 A | 1/2018 |
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 3034011 A1 | 6/2016 |
| EP | 3289984 A1 | 3/2018 |
| FR | 2 849 589 A1 | 7/2004 |
| WO | 20199414129 A1 | 6/1994 |
| WO | 20199729694 A1 | 8/1997 |
| WO | 20199740760 A1 | 11/1997 |
| WO | 20199837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004/032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-on-Line, Electronic Component Manufacturers, pp. 1-2; Aug. 2013.

Extended European Search Report dated Dec. 13, 2019 issued in corresponding EP Appln. No. 19188040.0.

Office Action issued in corresponding Chinese Application No. 201910661529.0 dated Apr. 11, 2023, together with English language transslation (10 pages).

Office Action issued in corresponding Japanese Application No. 2019-131092 mailed May 10, 2023, together with English language translation (16 pages).

\* cited by examiner

ADAPTIVE ANTI-TWITCH ALGORITHM FOR POWERED SURGICAL DEVICES

CROSS-REFERENCE TO RELATED APPLICATIONS

This application claims the benefit of and priority to U.S. Provisional Patent Application No. 62/702,995 filed Jul. 25, 2018, the entire disclosure of which is incorporated by reference herein.

BACKGROUND

1. Technical Field

The present disclosure relates to surgical devices. More specifically, the present disclosure relates to powered surgical devices with articulating loading units.

2. Background of Related Art

Surgical fastener devices for applying fasteners or staples to tissue are well known. These fastener devices include single-use devices which are preloaded with one or more staples and are disposable after a single use. Multiple use devices are also available and are preloaded with a plurality of staples. Multiple use devices may include a handle assembly that is electromechanically, e.g., powered, or manually actuated. These devices may be used with single use loading units (SULU) or multiple use loading units (MULU). The loading units include a body and an end effector, and are attached to the handle assembly, either directly or via an adapter assembly couplable to the handle assembly. The loading units may also include an articulating end effector. In powered surgical devices, which utilize motors to actuate and/or articulate the end effector, the motors may inadvertently cause unwanted movement of the end effector. Accordingly, there is a need for powered surgical devices that minimize and/or mitigate the effects of inadvertent movement.

SUMMARY

According to one embodiment of the present disclosure, a surgical device includes a handle assembly having a controller; a first motor; and a second motor. The surgical device also includes an adapter assembly having: a tubular housing defining a longitudinal axis having a proximal end portion configured to couple to the handle assembly, and a distal end portion; a first actuation assembly disposed within the tubular housing and coupled to the first motor; and a second actuation assembly disposed within the tubular housing and coupled to the second motor. The surgical device further includes an end effector configured to couple to the distal end portion of the adapter assembly. The end effector is coupled to the first actuation assembly that articulates the end effector about an articulation axis that is perpendicular to the longitudinal axis. The end effector also includes a flexible drive beam coupled to the second actuation assembly and movable axially by the second actuation assembly. The controller is configured to maintain an initial articulation position of the end effector in response to axial movement of the flexible drive beam.

According to one aspect of the above embodiment, the end effector includes an anvil assembly and a cartridge assembly. The flexible drive beam is configured to move axially through the anvil assembly and the cartridge assembly to pivot the anvil assembly relative to the cartridge assembly.

According to another aspect of the above embodiment, the controller is further configured to adjust the first motor to compensate for a change in the initial articulation position due to movement of the flexible drive beam.

According to a further aspect of the above embodiment, the controller includes a memory and stores the initial articulation position of the end effector in the memory. The controller is further configured to compensate for a change in the initial articulation position due to movement of the flexible drive beam to maintain the initial articulation position. The memory stores a database having a plurality of articulation correction values, each of which corresponds to one of a plurality of longitudinal position values of the flexible drive beam. The controller is further configured to adjust the first motor based on an articulation correction value corresponding to a longitudinal position value. The controller is further configured to determine the longitudinal position value based on rotation of the second motor.

According to yet another aspect of the above embodiment, the surgical device further includes an articulation sensor configured to obtain a measured articulation position of the end effector. The controller is further configured to adjust the first motor based on the measured articulation position.

According to another embodiment of the present disclosure, a method for controlling a surgical device includes operating a first motor to actuate a first actuation assembly configured to articulate an end effector to an initial articulation position; operating a second motor to actuate a second actuation assembly configured to move a flexible drive beam through the end effector; and maintaining the initial articulation position by adjusting the first motor in response to actuation of the second actuation assembly and movement of the flexible drive beam.

According to one aspect of the above embodiment, the method further includes measuring an articulation position of the end effector during movement of the flexible drive beam to obtain a measured articulation position. The method further includes adjusting the first motor to compensate for a change in the initial articulation position based on the measured articulation position.

According to another aspect of the above embodiment, the method further includes: storing a database having a plurality of articulation correction values, each of which corresponds to one of a plurality of longitudinal position values of the flexible drive beam. The method further includes adjusting the first motor based on an articulation correction value corresponding to a longitudinal position value and determining the longitudinal position value based on rotation of the second motor.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure provides a powered surgical device including a handle assembly, a loading unit, which is interconnected to the handle assembly via an adapter assembly. The loading unit includes an end effector, which is configured to articulate about an articulation axis that is perpendicular to a longitudinal axis defined by the adapter assembly. The end effector includes a pair of jaw members—an anvil assembly and a cartridge assembly including staples. In embodiments, the end effector may articulate up to about 45 degrees relative to the longitudinal axis in either direction. The handle assembly includes one or more motors which are configured to actuate the end effector, including its articulation, in response to clinician's inputs, such as pressing a switch corresponding to desired articulation direction.

Initially, the clinician orients the end effector into a desired position, e.g., by rotating the adapter assembly and/or articulating the end effector. After the end effector is disposed about desired tissue region, the clinician actuates the end effector to clamp about the tissue, eject staples into the tissue and cut the tissue by advancing a flexible drive beam through the end effector. After the stapling and cutting is completed, the flexible drive beam is retracted to open the jaw members and release the tissue.

During retraction, the flexible drive beam may inadvertently change the articulation position of the end effector due to the lateral forces imparted on the end effector by the flexible drive beam. Thus, rather than remaining stationary during retraction of the flexible drive beam, the end effector is unintentionally moved, i.e., "twitches." This twitching may be approximately 13.5 degrees on average depending on the original angle of articulation. Furthermore, when the end effector is articulated to the left, which may be accomplished by moving an articulation link of the adapter assembly proximally (e.g., pulling the articulation link), the retraction twitch may increase in conjunction with an increase in the distance that the articulation link has been moved. When the end effector is articulated to the right, which is accomplished by moving the articulation link distally (e.g., pushing the articulation link), the retraction twitch causes a quick increase in push articulation, followed by a gradual decrease in articulation back to the originally set articulation position. The cause of the change in articulation may be due to a net moment in the jaws caused by the bending of the flexible drive beam during articulation.

The present disclosure provides for a system and method to counteract the net moment in the end effector by controlling an articulation motor during retraction of the flexible drive beam. The handle assembly includes a controller which controls operation of the articulation motor and a firing motor. The controller is configured to execute software including a set of computer-readable instructions, which embody an anti-twitch algorithm. The adapter assembly includes a load sensing assembly, such as a strain gauge, configured to measure strain imparted on the articulation actuation assembly during retraction of the flexible drive beam to provide feedback to the controller. The controller then corrects for the detected twitch due to the retraction by operating the articulation motor to compensate for the twitching in a closed-loop control scheme.

In another embodiment, the controller may operate the articulation motor without relying on closed-loop control scheme and instead utilizing data including a correction factor corresponding to an articulation angle of the end effector. The data may be collected empirically or derived. For each articulation position as well as the longitudinal position of the flexible drive beam the data includes a preset correction factor, allowing the controller to estimate the amount of movement the articulation motor would move the articulation link to compensate for the twitch. Thus, an open loop control scheme may be based on collected data including changes in articulation position corresponding to initial articulation at the start of firing.

The handle assembly is also configured to maintain the articulation position of the end effector during firing (e.g., movement in the distal direction) of the flexible drive beam as well as during the retraction of the drive beam. While using the closed loop algorithm based on sensor feedback for pull (e.g., left) articulation, the handle assembly gradually reduces the degree of articulation during firing and quickly restores the degree of articulation to its initial firing position during retraction. Using the open loop control scheme, the articulation position may be adjusted during retraction or firing using a preprogramed anti-twitch pattern corresponding to the collected data.

Figure 1:
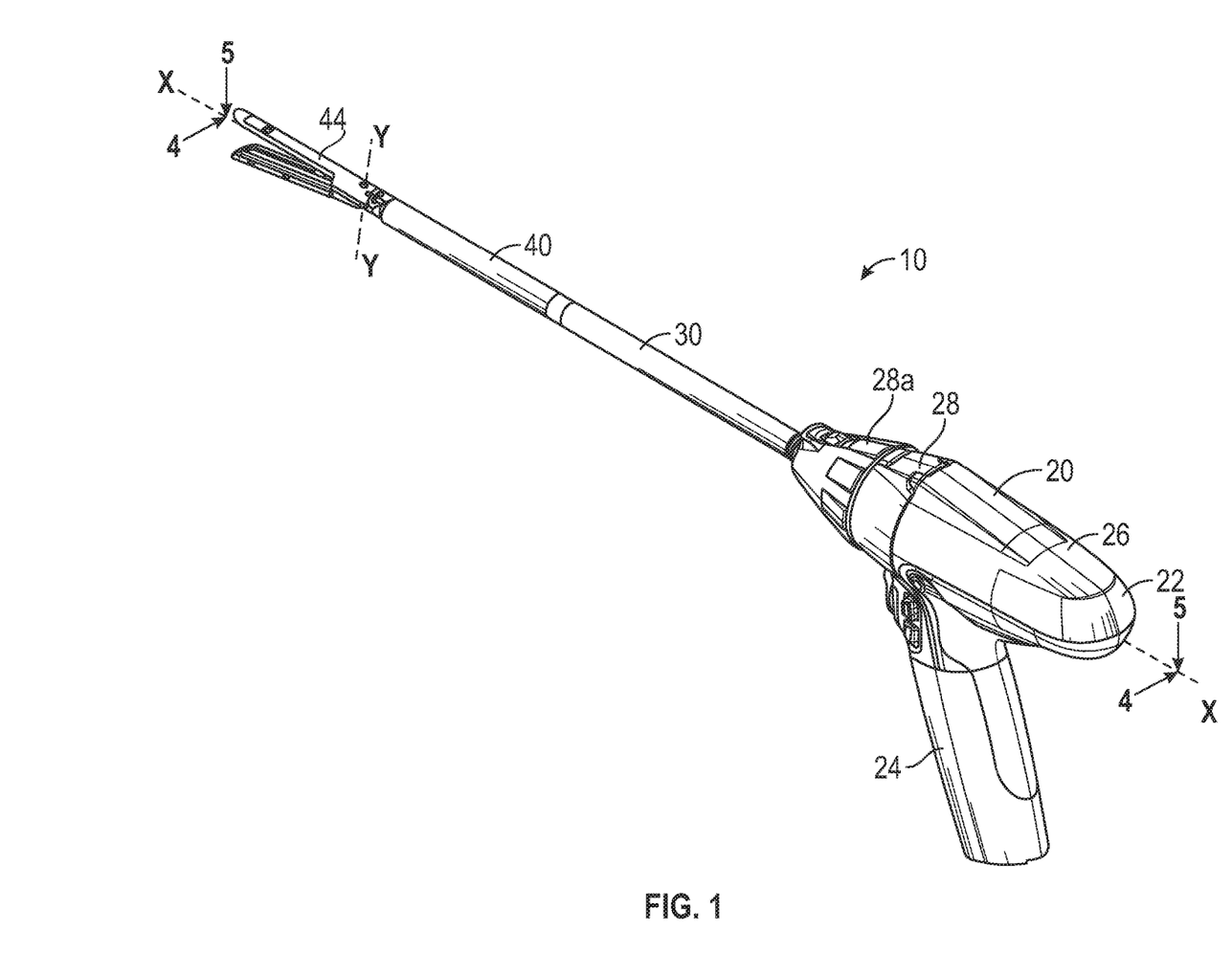
FIG. 1 is a perspective view of a handheld surgical device, an adapter assembly, and a surgical loading unit according to an embodiment of the present disclosure.

With reference to FIG. 1, a powered surgical device 10 includes a handle assembly 20, which is configured for selective connection with an adapter assembly 30, which in turn, is configured for selective connection with a loading unit 40 having an end effector 44. Although generally referred to as being a powered surgical device, it is contemplated that the surgical device 10 may be manually actuated and may include various configurations.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. The handle assembly 20 also includes a plurality of controls 23, which may include buttons, touchscreen, or any other user input devices, for allowing the clinician to control the operation of the surgical device 10.

Figure 2:
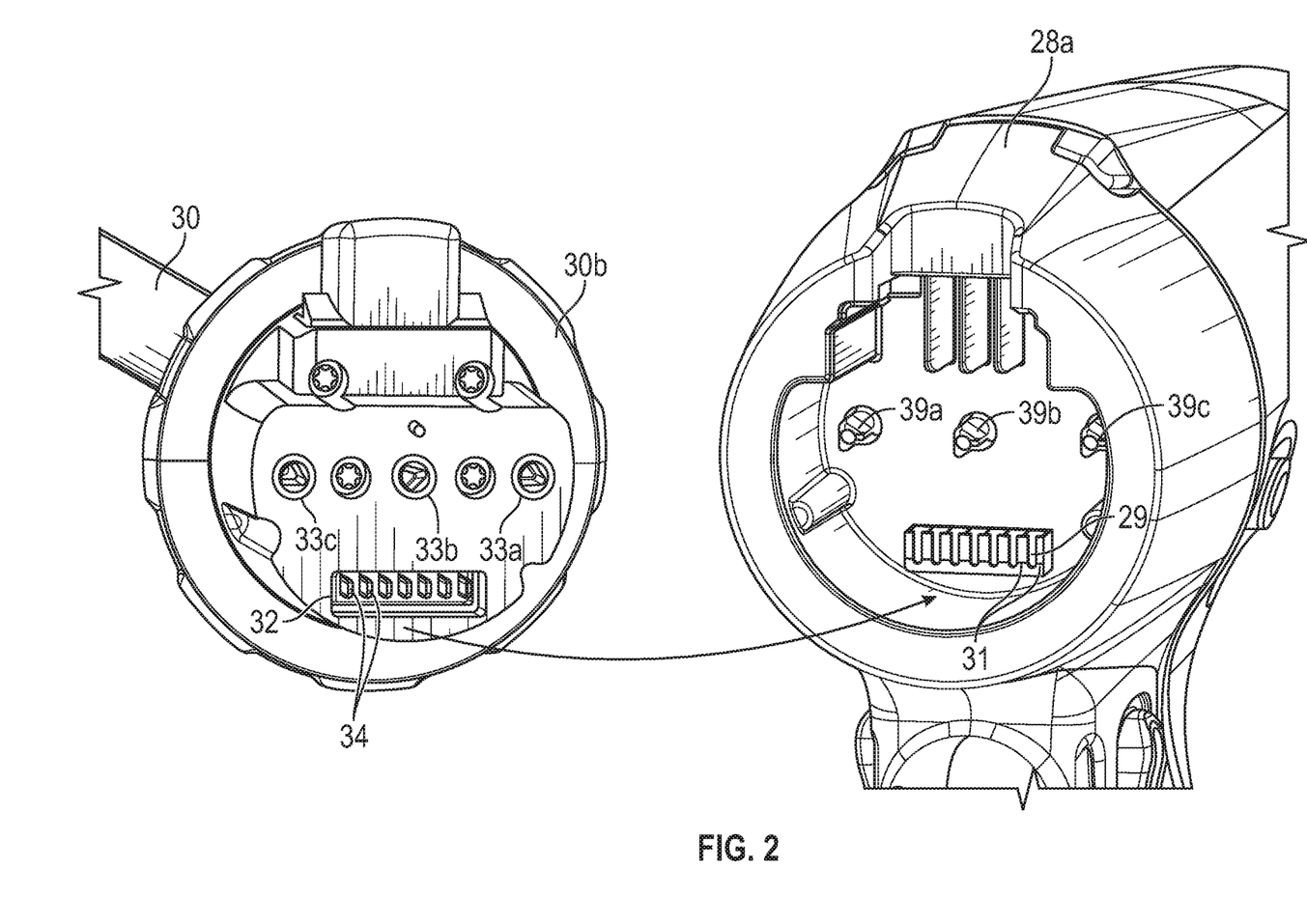
FIG. 2 is a perspective view illustrating a connection of the adapter assembly and the handle assembly of FIG. 1 according to an embodiment of the present disclosure.
Figure 3:
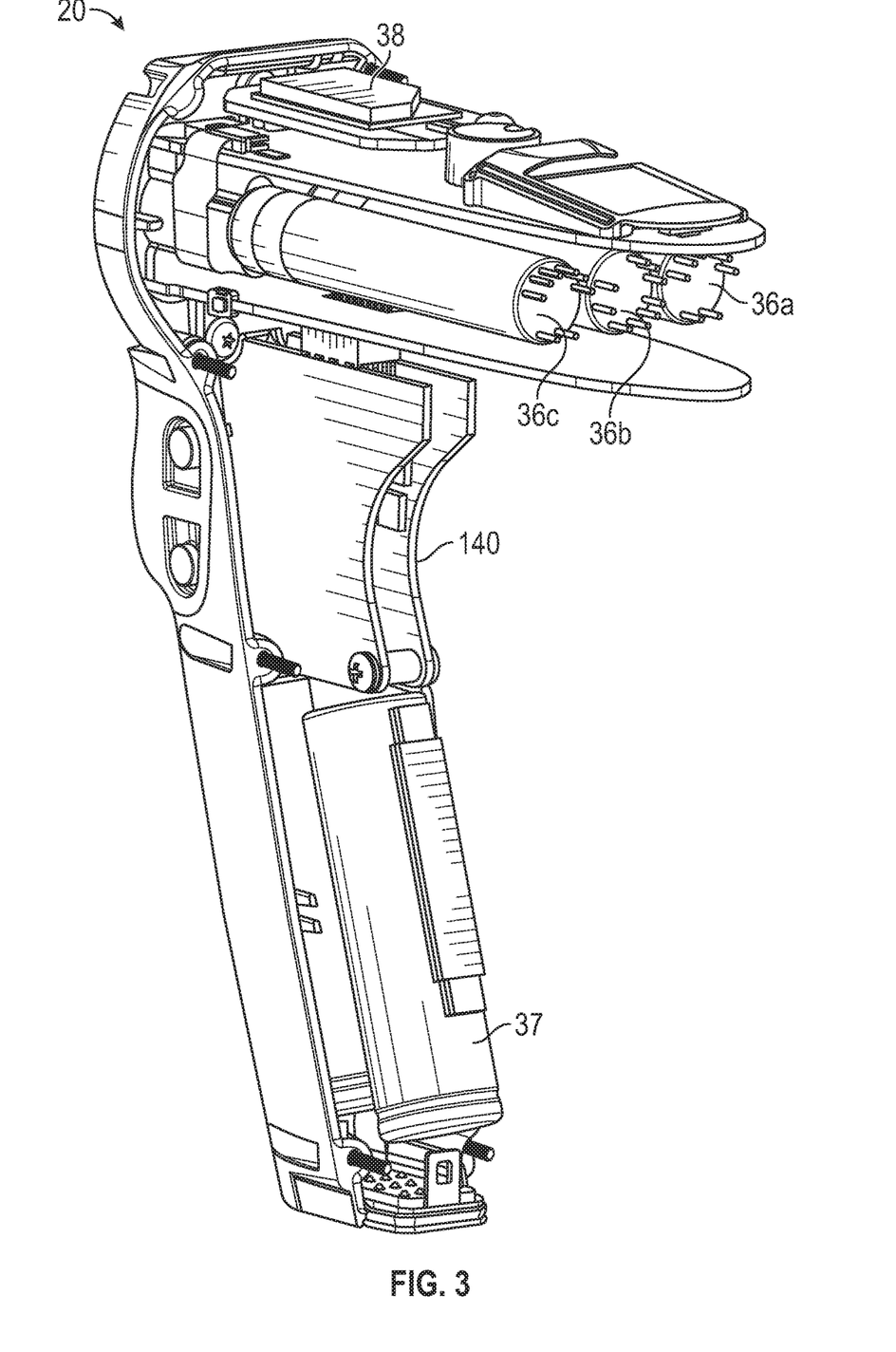
FIG. 3 is perspective view of internal components of the handle assembly according to an embodiment of the present disclosure.

As shown in FIG. 2, a distal portion of the upper housing portion 28 defines a nose or connecting portion 28a that is configured to accept a proximal end portion 30b of the adapter assembly 30. The connecting portion 28a of the upper housing portion 28 includes an electrical receptacle 29 having a plurality of electrical contacts 31, which are in electrical communication with electronic (e.g., controller 38) and electrical components (e.g., power source 37) of the handle assembly 20 (FIG. 3). The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 3, the handle assembly 20 includes motors 36a, 36b, 36c which are coupled to a power source 37. The handle assembly 20 also includes a controller 38 for operating the motors 36a, 36b, 36c and other electronic components of the handle assembly 20, the adapter assembly 30, and the loading unit 40. The motors 36a, 36b, 36c are coupled to corresponding drive shafts 39a, 39b, 39c (FIG. 2), which are configured to engage respective sockets 33a, 33b, 33c on the proximal end portion 30b, such that rotation of the drive shafts 39a, 39b, 39c is imparted on the sockets 33a, 33b, 33c.

The controller 38 may include any suitable logic controller (e.g., FPGA) and a memory storing software instructions executable by the logic controller to operate the motors 36a, 36b, 36c as well as other components of the surgical device 10. The memory of the controller 38 may also store various data in addition to software instructions. The controller 38 is also coupled to the controls 23 and is configured to operate the motors 36a, 36b, 36c in response to user inputs through the controls 23.

Figure 4:
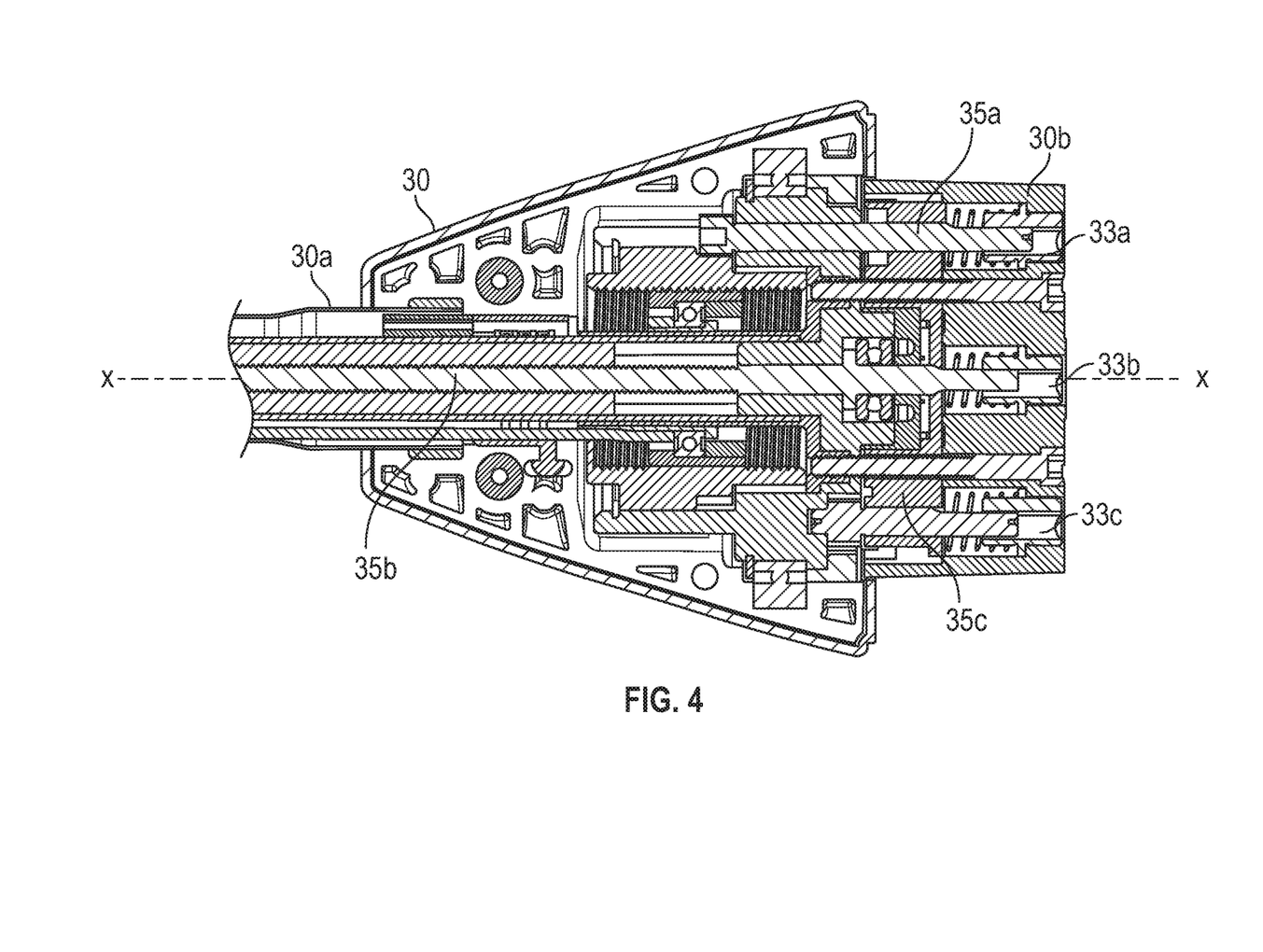
FIG. 4 is cross-sectional view of the adapter assembly taken along a section plane "4-4" of FIG. 1 according to an embodiment of the present disclosure.
Figure 5:
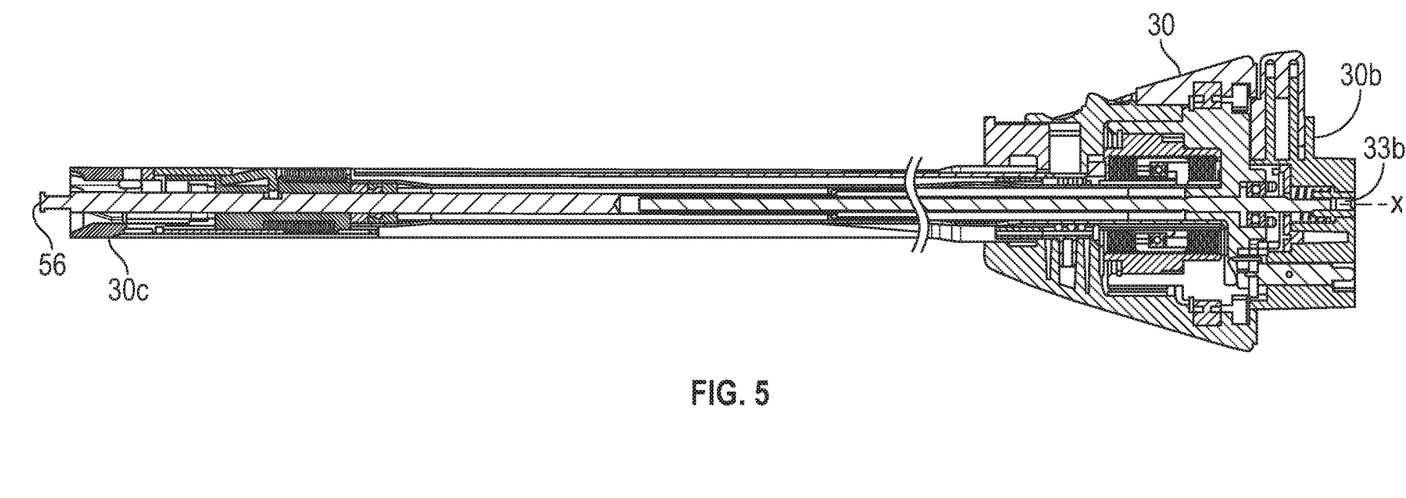
FIG. 5 is cross-sectional view of the adapter assembly taken along a section plane "5-5" of FIG. 1 according to an embodiment of the present disclosure.
Figure 6:
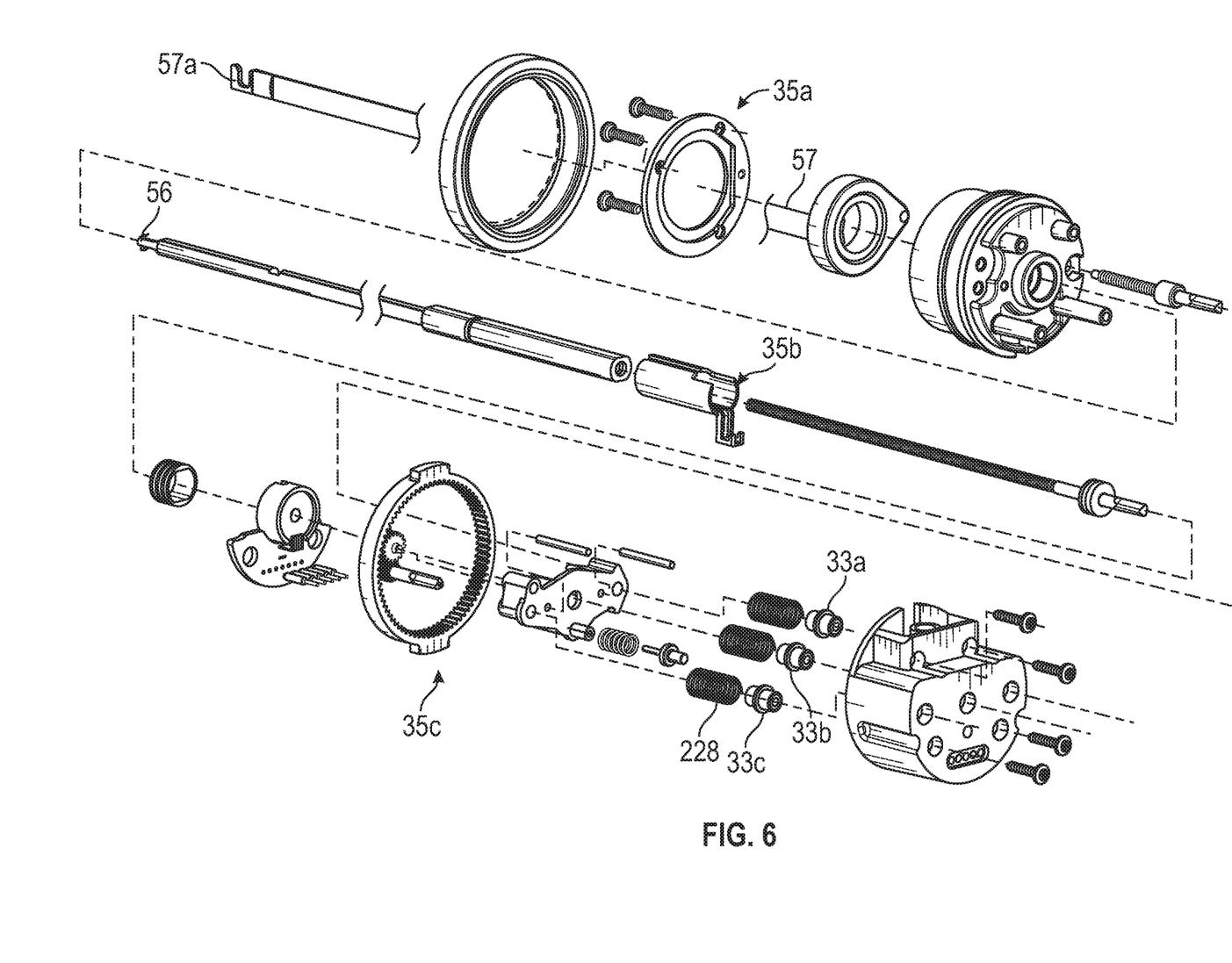
FIG. 6 is a perspective view, with parts separated, of the adapter assembly of FIG. 1 according to an embodiment of the present disclosure.

With reference to FIGS. 4-6, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the loading unit 40. The adapter assembly 30 includes actuation assemblies 35a, 35b, 35c each of which is coupled to one of the sockets 33a, 33b, 33c (FIG. 6). The actuation assemblies 35a, 35b, 35c are configured to transfer rotational motion of the sockets 33a, 33b, 33c into linear motion and/or rotational motion, such that the adapter assembly 30 is configured to convert a rotational motion provided by the handle assembly 20 into axial translation for rotating the adapter assembly 30 about a longitudinal axis X-X, articulate the loading unit 40, clamp tissue, eject fasteners, and cut fastened tissue.

With reference to FIG. 6, the actuation assembly 35a includes an articulation link 57 having a hook 57a disposed at a distal end portion of the articulation link 57. Longitudinal movement of the articulation link 57 is used to articulate the end effector 44 about an articulation axis Y-Y (FIGS. 1 and 7), which is perpendicular to the longitudinal axis X-X. The actuation assembly 35b includes a drive member 56, which is used to operate an anvil assembly 46 and a cartridge assembly 48 of the end effector 44. The actuation assembly 35c is used to rotate the adapter assembly 30 about the longitudinal axis X-X.

As shown in FIG. 5, the adapter assembly 30 also includes an articulation sensor 61 disposed within the tubular housing 30a. The articulation sensor 61 may be any device configured to sense the articulation position of the end effector 44 relative to the longitudinal axis X-X. In embodiments, the articulation sensor 61 may be an encoder configured to measure the travel distance of the actuation assembly 35a or any other mechanical linkages responsible for articulation. In further embodiments, the articulation sensor 61 may be a proximity sensor configured to measure a distance between a point on the end effector 44 and the adapter assembly 30. The end effector 44 may include a magnet 61a (FIG. 7) and the articulation sensor 61 may include a Hall Effect sensor which outputs a sensor signal based on the distance of the magnet 61a.

The articulation sensor 61 is coupled to controller 38 through the electrical connector 32 that is configured to engage the electrical receptacle 29. This allows the articulation sensor 61 to transmit a sensor signal corresponding to the articulation position. The controller 38 may utilize the sensor signal as a feedback parameter in a closed-loop control scheme.

Figure 7:
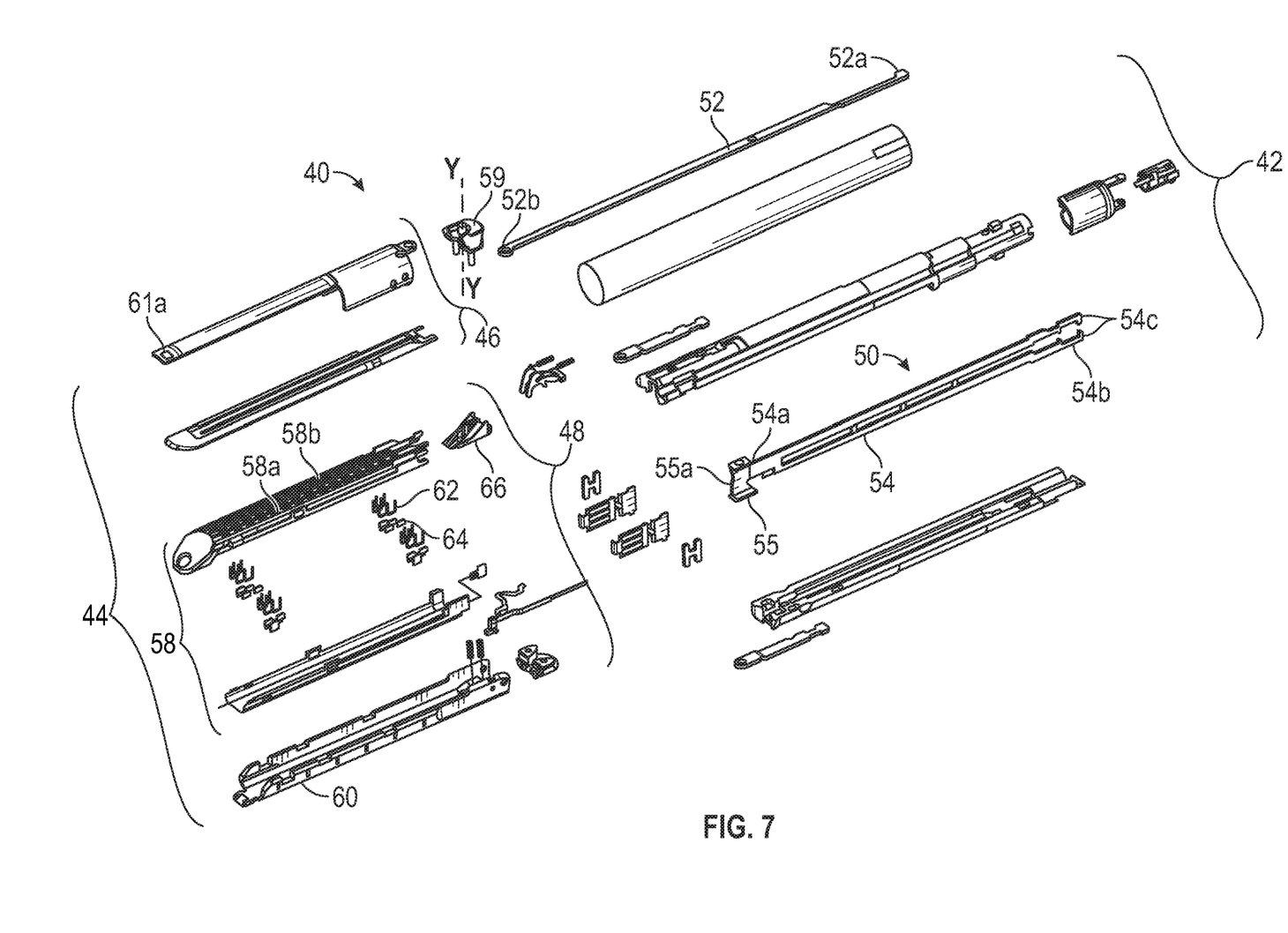
FIG. 7 is a perspective view, with parts separated, of the surgical loading unit of FIG. 1 according to an embodiment of the present disclosure.

With reference to FIGS. 1 and 7, an embodiment of the loading unit 40 is shown. The loading unit 40 includes a proximal body portion 42 and the end effector 44. Proximal body portion 42 is releasably attached to the distal end portion 30c of adapter assembly 30, and end effector 44 is pivotally attached to a distal end of proximal body portion 42. End effector 44 includes the anvil assembly 46 and the cartridge assembly 48. Anvil assembly 46 is pivotable in relation to the cartridge assembly 48 and is movable between an open or unclamped position and a closed or clamped position. Proximal body portion 42 includes a drive assembly 50 and an articulation link 52.

Drive assembly 50 includes a flexible drive beam 54 having a distal end portion 54a and a proximal engagement section 54b. The distal end portion 54a includes an I-beam 55 having a knife 55a. The I-beam 55 is configured to travel through the anvil assembly 46 and the cartridge assembly 48, thereby pushing the anvil assembly 46 toward the cartridge assembly 48 to clamp tissue. The proximal engagement section 54b includes diametrically opposed inwardly extending fingers 54c that engage the drive member 56 (FIGS. 5 and 6) to fixedly secure drive member 56 to the proximal end of flexible drive beam 54. Drive member 56 is actuated by the actuation assembly 35b of adapter assembly 30.

Cartridge assembly 48 of end effector 44 includes a staple cartridge 58 removably supported in a carrier 60. Staple cartridge 58 defines a central longitudinal slot 58a, and a plurality of linear rows of staple retention slots 58b positioned on each side of the central longitudinal slot 58a. Each of the staple retention slots 58b receives a single staple 62 and a portion of a staple pusher 64. During operation of the surgical device 10, drive assembly 50 abuts an actuation sled 66 and pushes actuation sled 66 through the staple cartridge 58. As the actuation sled 66 moves through staple cartridge 58, cam wedges of the actuation sled 66 sequentially engage staple pushers 64 to move staple pushers 64 vertically within staple retention slots 58*b* and sequentially eject a single staple 62 therefrom for formation against an anvil plate 46*a* of anvil assembly 46.

Proximal body portion 42 of loading unit 40 includes an articulation link 52 having a hooked proximal end portion 52*a* which extends from a proximal end of loading unit 40 which engages the opposing articulation link 57 coupled to the actuation assembly 35*a* of the adapter assembly 30. Articulation link 52 has a distal end portion 52*b* pivotably secured to end effector 44. As the articulation link 57 is moved in an axial direction by the actuation assembly 35*a* of the adapter assembly 30, either proximally or distally, the articulation link 52 of the loading unit 40 is also moved in the same manner. Axial movement of the articulation link 52, in turn, articulates (e.g., pivots) the end effector 44 about a pivot pin 59, which defines the axis Y-Y.

Figure 8:
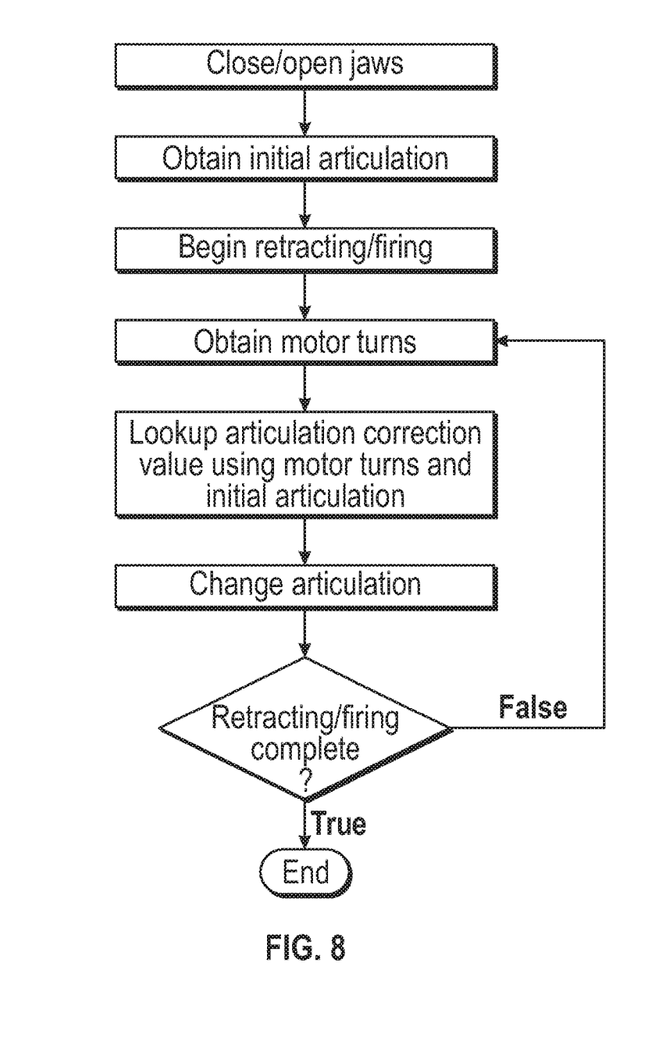
FIG. 8 is a flow chart of a method for operating the surgical device to compensate for undesired movement of the end effector during firing or retraction according to one embodiment of the present disclosure.

With reference to FIG. 8, a method for operating the surgical device 10 for compensating for undesired movement of the end effector 44 during firing or retraction of the flexible drive beam 54 is shown. The method may be embodied as software or any other computer-readable instructions stored in the memory of the controller 38. Initially, the clinician actuates the controls 23 to orient the end effector 44 in a desired position, which may include rotating the adapter assembly 30 and/or articulating the end effector 44 relative to the axis X-X. Once the end effector is in the desired position, the clinician actuates the controls 23 to open or close the anvil assembly 46. In embodiments, the clinician may actuate the controls 23 to fire or retract the flexible drive beam 54, which includes initially opening or closing the anvil assembly 46. In embodiments, the method is also suitable for compensating for unwanted movement of the end effector 44 during retraction of the flexible drive beam 54. Positioning of the end effector 44 would not be necessary as the end effector 44 would be clamped about tissue.

After actuating the controls 23, the controller 38 moves actuation assembly 35*b* to open or close the anvil assembly 46 by moving the actuating assembly 35*b*. More specifically, the controller 38 instructs the motor 36*b* to rotate a predetermined number of revolutions to open or close the anvil assembly 46. Once the anvil assembly 46 has been opened or closed, the controller 38 then obtains an initial articulation position. The controller 38 may interrupt movement of the actuation assembly 35*b* to obtain the articulation position. In embodiments, the initial articulation position may be the last stored articulation position, which is stored in memory of the controller 38. More specifically, the controller 38 continuously records the articulation position, which corresponds to the number of rotations of the motor 36*a*, which operates the actuation assembly 35*a* for articulating the end effector 44. This allows the controller 38 to continuously track the articulation position, as such the last recorded articulation position may be used as an initial articulation position for the purposes of this method.

Once the initial articulation position is saved in the memory, the controller 38 proceeds to fire or retract the flexible drive beam 54. As the actuation assembly 35*b* is moved, the controller 38 compensates for the changes in the articulation position of end effector 44 based on the current position of the flexible drive beam 54. The controller 38 stores in the memory a database of articulation correction values for adjusting the position of the motor 36*a*, which is responsible for moving the actuation assembly 35*a* to articulate the end effector 44. The database also includes a plurality of position values of the motor 36*b*, which is responsible for moving the actuation assembly 35*b*, which moves the flexible drive beam 54 during firing or retraction. Each of the position values of the flexible drive beam 54 corresponds to the articulation correction values in the database. In the database, the articulation correction values may be obtained by measuring the changes in the articulation position during firing and retraction of the flexible drive beam 54. In additional embodiments, the articulation correction values may be derived using transfer functions correlating firing and/or retraction movements with articulation positions.

As the flexible drive beam 54 is moved, the controller 38 adjusts the position of the actuation assembly 35*a* based on the corresponding articulation correction value. More specifically, the controller 38 compensates for the changes in the articulation position of the end effector 44 due to the movement of the actuation assembly 35*b* (responsible for moving the flexible drive beam 54) by moving the actuation assembly 35*a* (responsible for articulating the end effector 44). For each rotation of the motor 36*b*, the controller 38*a* instructs the motor 36*a* to actuate the actuation assembly 35*a* based on the articulation correction values, which provide the number of rotations for motor 36*a*. As the flexible drive beam 54 is moved, the controller 38 continues to adjust the articulation position based on the database until firing or retraction of the flexible drive beam 54 is completed.

Figure 9:
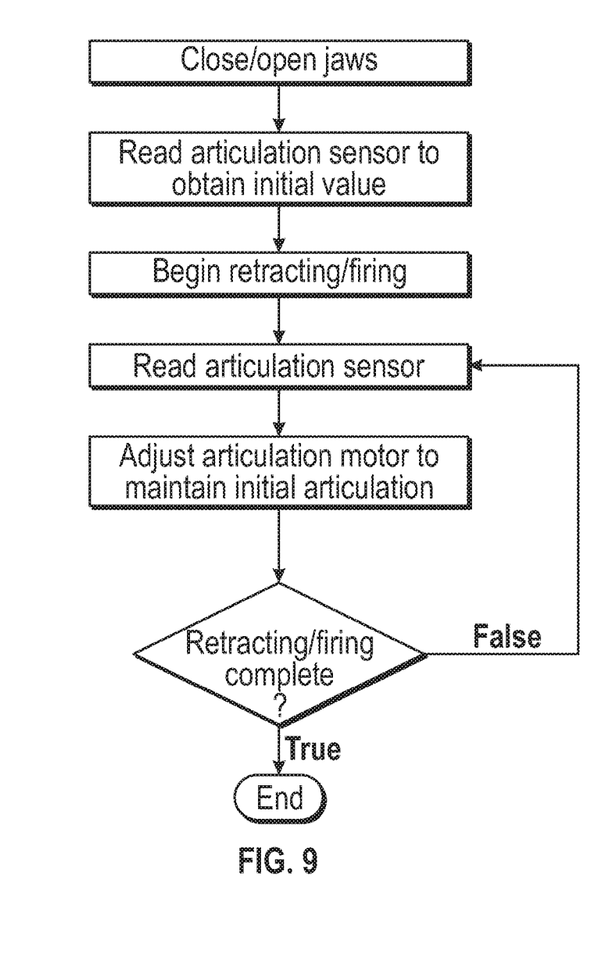
FIG. 9 is a flow chart of a method for operating the surgical device to compensate for undesired movement of the end effector during firing or retraction according to another embodiment of the present disclosure.

FIG. 9 shows another method for compensating for operating the surgical device 10 due to undesired movement of the end effector 44 during firing or retraction of the flexible drive beam 54. The method of FIG. 9 utilizes sensor signals from the articulation sensor 61 to move the motor 36*a* thereby moving the actuation assembly 35*a* and compensating for the undesired movement of the end effector 44. The method of FIG. 9 is similar to the method of FIG. 8 and only the differences are described below.

After actuating the controls 23 to close or open the anvil assembly 46, the controller 38 moves actuation assembly 35*b* to open or close the anvil assembly 46 by moving the actuating assembly 35*b*. Once the anvil assembly 46 has been opened or closed, the controller 38 then obtains an initial articulation position by querying the articulation sensor 61 to obtain the articulation position. The controller 38 may interrupt movement of the actuation assembly 35*b* to obtain the initial articulation position.

Once the initial articulation position is saved in the memory, the controller 38 proceeds to fire or retract the flexible drive beam 54. As the actuation assembly 35*b* is moved, the controller 38 compensates for the changes in the articulation position of end effector 44 based on changes in the articulation position of the end effector 44 according to the readings from the articulation sensor 61. As the flexible drive beam 54 is moved, the controller 38 compensates for the changes in the articulation position of the end effector 44 due to the movement of the actuation assembly 35*b* (responsible for moving the flexible drive beam 54) by moving the actuation assembly 35*a* (responsible for articulating the end effector 44). As the flexible drive beam 54 is moved, the controller 38 continues to adjust the articulation position based on the database until firing or retraction of the flexible drive beam 54 is completed.

In embodiments, the methods of FIGS. 8 and 9 may be combined in any suitable manner, such that the surgical device 10 utilizes the database of articulation correction values as well as the articulation sensor 61 to provide for a hybrid compensation method. It is envisioned, that the articulation sensor 61 may be used to obtain the initial articulation position of the end effector 44 and utilize the database in conjunction with the readings from the articulation sensor 61 to make adjustments to the motor 36*a*. Alternatively, the initial articulation reading may be taken by using the last stored articulation position and using only the articulation sensor 61 to make adjustments.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical device comprising:
    a handle assembly including:
        a controller;
        an articulation motor; and
        a firing motor;
    an adapter assembly including:
        a tubular housing defining a longitudinal axis having a proximal end portion configured to couple to the handle assembly, and a distal end portion;
        a articulation actuation assembly disposed within the tubular housing and coupled to the articulation motor; and
        a firing actuation assembly disposed within the tubular housing and coupled to the firing motor; and
    an end effector configured to couple to the distal end portion of the adapter assembly, the end effector coupled to the articulation actuation assembly that articulates the end effector about an articulation axis that is perpendicular to the longitudinal axis, the end effector includes a flexible drive beam coupled to the firing actuation assembly and movable axially by the firing actuation assembly;
    wherein the controller is configured to:
        maintain an initial articulation position of the end effector in response to axial movement of the flexible drive beam;
        measure current articulation position; and
        adjust the articulation motor to compensate for a change in the initial articulation position based on the current articulation position due to movement of the flexible drive beam by the firing motor.

2. The surgical device according to claim 1, wherein the end effector includes an anvil assembly and a cartridge assembly.

3. The surgical device according to claim 2, wherein the flexible drive beam is configured to move axially through the anvil assembly and the cartridge assembly to pivot the anvil assembly relative to the cartridge assembly.

4. The surgical device according to claim 1, wherein the controller includes a memory and stores the initial articulation position of the end effector in the memory, the controller is further configured to compensate for the change in the initial articulation position due to movement of the flexible drive beam to maintain the initial articulation position.

5. The surgical device according to claim 4, wherein the memory stores a database having a plurality of articulation correction values, each of which corresponds to one of a plurality of longitudinal position values of the flexible drive beam.

6. The surgical device according to claim 5, wherein the controller is further configured to adjust the articulation motor based on an articulation correction value corresponding to a longitudinal position value.

7. The surgical device according to claim 5, wherein the controller is further configured to determine the longitudinal position value based on rotation of the firing motor.

8. The surgical device according to claim 4, further comprising an articulation sensor configured to obtain a measured articulation position of the end effector.

9. The surgical device according to claim 8, wherein the controller is further configured to adjust the articulation motor based on the measured articulation position.

* * * * *